US00PP25670P3

(12) United States Plant Patent
Ponto

(10) Patent No.: US PP25,670 P3
(45) Date of Patent: Jun. 30, 2015

(54) ***LIRIOPE GIGANTEA* PLANT NAMED 'PONTOVIA'**

(50) Latin Name: *Liriope gigantea*
Varietal Denomination: Pontovia

(71) Applicant: Robert Ponto, Vista, CA (US)

(72) Inventor: Robert Ponto, Vista, CA (US)

( * ) Notice: Subject to any disclaimer, the term of this patent is extended or adjusted under 35 U.S.C. 154(b) by 171 days.

(21) Appl. No.: 13/986,954

(22) Filed: Jun. 18, 2013

(65) Prior Publication Data

US 2014/0373239 P1 Dec. 18, 2014

(51) Int. Cl.
*A01H 5/00* (2006.01)

(52) U.S. Cl.
USPC ..... Plt./450

(58) Field of Classification Search
USPC ..... Plt./450
See application file for complete search history.

*Primary Examiner* — Annette Para
(74) *Attorney, Agent, or Firm* — Samuel R. McCoy, Jr.

(57) ABSTRACT

'Pontovia' is a distinctive variety of *Liriope gigantea* which is characterized by the combination of: foliage variegation ranging from gold striations at and near the leaf margins with lime-green striations concentrated at or near the leaf midrib in immature foliage, to near-silver striations at and near the leaf margins with dark green striations concentrated at and near the leaf midrib in mature foliage and varying amounts of each color at intermediate stages of leaf development; dark violet flowers; and taller inflorescences.

3 Drawing Sheets

Latin name of the genus and species: The Latin name of the genus and species of the novel variety disclosed herein is *Liriope gigantea*.

Variety denomination: The inventive variety of *Liriope gigantea* disclosed herein has been given the variety denomination 'Pontovia'.

BACKGROUND OF THE INVENTION

The present invention relates to a new and distinct perennial variety of *Liriope gigantea*, which has been given the variety denomination of 'Pontovia'. Its market class is that of an ornamental flowering perennial. 'Pontovia' is intended for use in landscaping and also in garden containers. *Liriope gigantea*, commonly called "giant lilyturf", is an evergreen perennial native to China and Japan that forms large clumps of dark green grass-like leaves with light lavender flower spikes that appear in summer. Its consistent size and performance through its hardiness range make it an ideal choice for specimen, borders and mass plantings in any filtered sun to shady, low-maintenance landscape or container.

Parentage: In 2006, seed that resulted from an open pollination of the species *Liriope gigantea* was sown at a wholesale nursery in Vista, Calif. The resulting progeny were potted into 15 cm nursery pots and placed in a production area to grow on to a mature, sellable size. While inspecting the crop in June of 2007, one plant was observed to have green and yellow, to green and white foliage variegation whereas the parent and other sibling progeny did not have variegated foliage; the plant was isolated for further observation. Said plant was further grown and asexually propagated through several generations from 2007 until July of 2012, at which time it was determined that the characteristics for which it was originally selected were uniform and stable. The new plant was given the name 'Pontovia'.

Asexual Reproduction: 'Pontovia' was first asexually propagated by dividing the root-bearing, rhizomatous propagules of the plant (i.e. "division cloning") in 2007 in Vista, Calif. and has since been asexually propagated through seven subsequent generations. The distinctive characteristics of the inventive 'Pontovia' variety are stable from generation to generation; clones of the variety produced by asexual reproduction maintain the distinguishing characteristics of the original plant.

SUMMARY OF THE INVENTION

'PONTOVIA' is a distinctive variety of *Liriope gigantea* which is characterized by the combination of: foliage variegation ranging from gold striations at and near the leaf margins with lime-green striations concentrated at or near the leaf midrib in immature foliage, to near-silver striations at and near the leaf margins with dark green striations concentrated at and near the leaf midrib in mature foliage and varying amounts of each color at intermediate stages of leaf development; dark violet flowers; and taller inflorescences.

BOTANICAL DESCRIPTION OF THE PLANT

Figure 1:
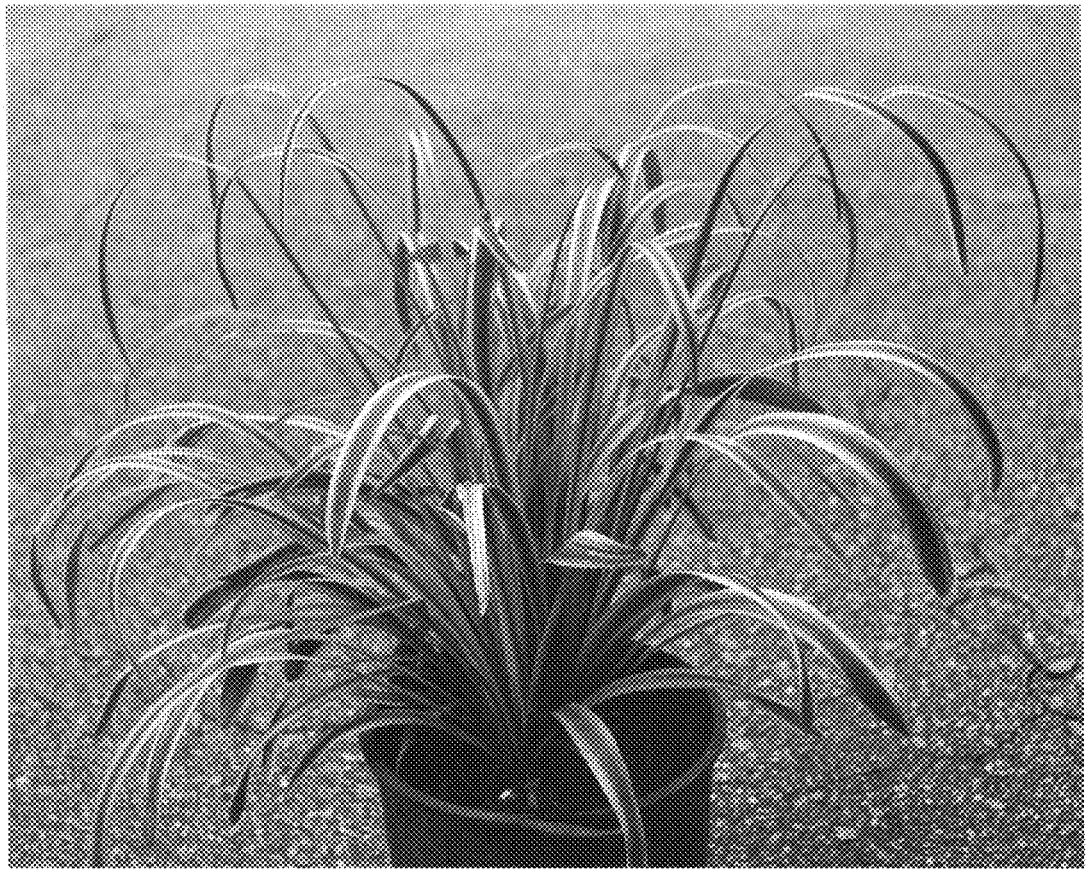
FIG. 1 shows an exemplary 'Pontovia' specimen, approximately 7 months of age, grown in a 15 cm nursery pot.
Figure 2:
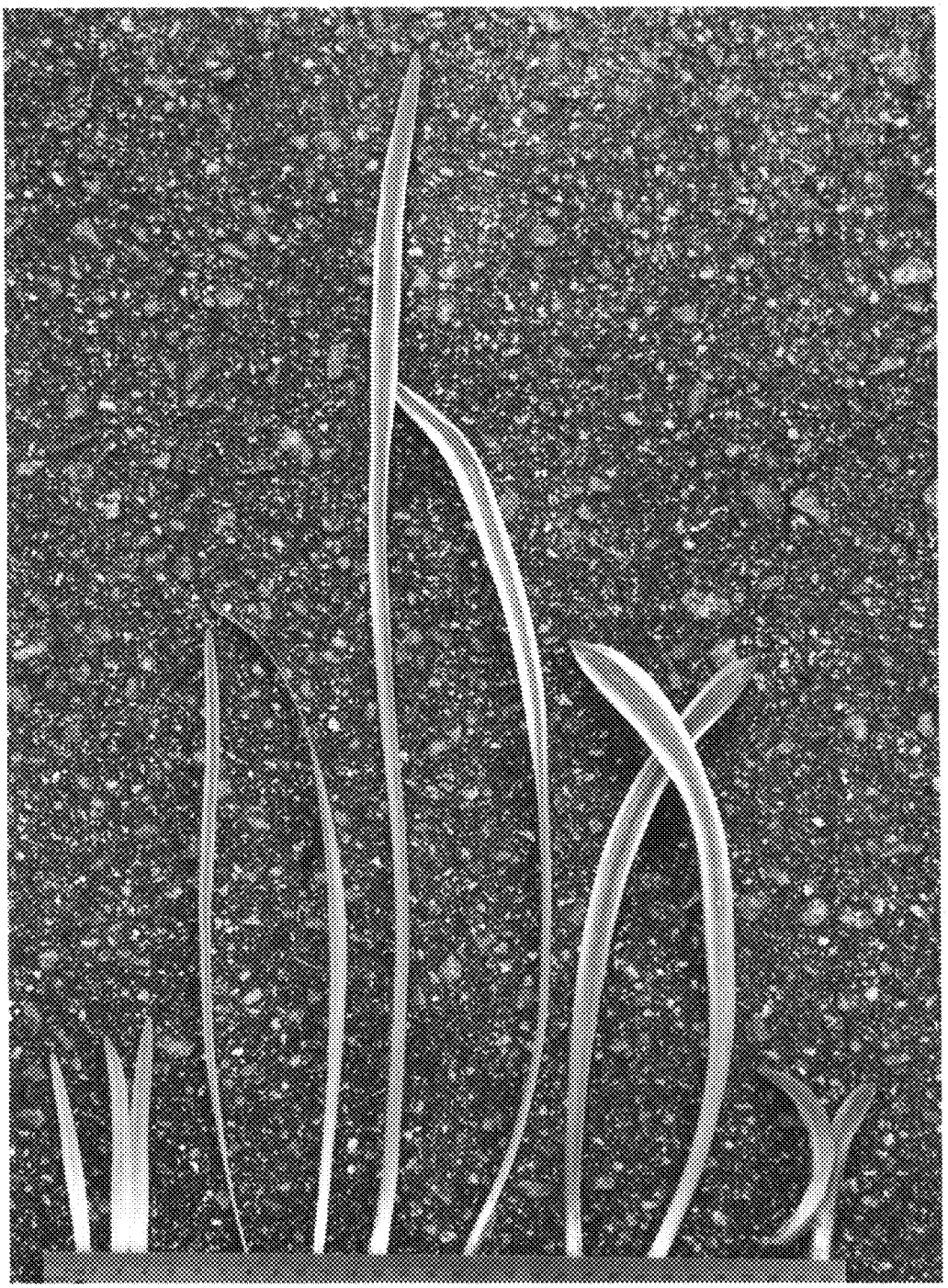
FIG. 2 shows the array of foliage variegation combinations of 'Pontovia', starting with immature shoots to the left and ending with the most mature foliage observed, on right.
Figure 3:
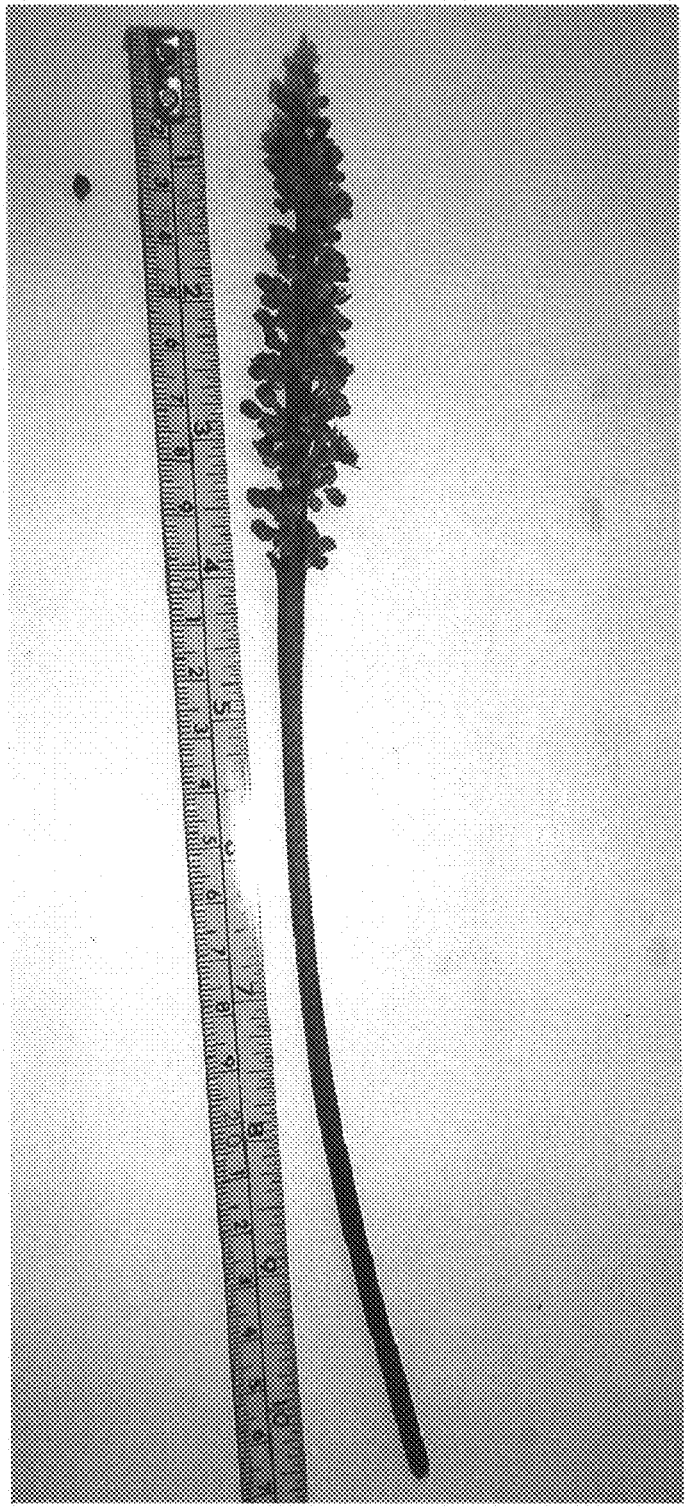
FIG. 3 shows an exemplary 'Pontovia' inflorescence. Of note is the long, dark violet peduncle and dark violet flower color.

The following is a detailed botanical description of a new and distinct variety of a *Liriope gigantea* ornamental plant known as 'Pontovia'. Plant observations were made on plants grown in Vista, Calif. Unless indicated otherwise, the descriptions disclosed herein are based upon observations made in June 2013 of mature 'Pontovia' plants, approximately 7 months of age, grown in soilless potting media in 15 cm nursery pots. Plants were grown under a shade structure; fertilized with slow release granular fertilizer and regularly watered with overhead irrigation. No pest or disease measures were taken during production.

Those skilled in the art will appreciate that certain characteristics will vary with older or, conversely, younger plants. 'Pontovia' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on *The Royal Horticultural Society Colour Chart*, The Royal Horticultural Society, London, 1986 edition. Note that generic color descriptions such as 'green' do not exist in the R.H.S. charts and the corresponding R.H.S. colors are quoted.

'Pontovia' is a selection of *Liriope gigantea* that is characterized by multicolored foliage variegation, dark violet flowers, and larger inflorescences. These features and other characteristics are apparent from the description provided below.

GROWTH HABIT, DIMENSIONS AND COLOR

Plant description:

*Plant habit.*—Rhizomatous herbaceous perennial with an arching habit and curled leaves.

*Height.*—30 cm, as measured.

*Width.*—45 cm, as measured.

*Bloom period.*—Summer.

*Hardiness.*—USDA Zone 6 to 10.

*Environmental tolerances.*—Prefers to be grown in partial shade. Drought tolerant once established; moderate to good recovery with watering after severe wilting. Tolerates a wide range of soil types from sandy loam to loamy clay.

*Pest and disease susceptibility or resistance.*—In common with the species, none of note.

*Propagation.*—Propagation is accomplished through division of rhizomes.

*Time to initiate roots.*—Approximately 2.5 weeks.

*Crop time.*—Depending on latitude of and microclimate of growing location, a fully rooted cutting requires approximately 3 months with an additional 5 to 7 months needed to produce a mature and marketable 15 cm container.

Roots: The roots of 'Pontovia' are fibrous and freely-branched, colored white, fleshy and thick with terminate tubers, similar to other *Liriope gigantea*; high root density. Very short and tightly clumped subsurface rhizomes which root at nodes.

Stem:

*Branching habit.*—Acaulescent, rhizomatous plant with shoots emerging from rhizomes with an upright attitude.

Basal shoots:

*Shoots density.*—7 divisions, or propagules, per 15 cm nursery pot, with the oldest propagules near the center of the plant's crown possessing 22 leaves and shoots of varying ages and sizes.

*Shoot strength.*—Medium.

*Cross section.*—Concave.

*Shoot color* (*adaxial surfaces*).—Variegated; comprised of yellow 2D striations at and near the margin and fine yellow-green 150B striations concentrated near the midrib; said yellow-green striations extending downward from shoot apex, eventually becoming indistinguishable near the basal half of the shoot, with basal portion of the shoot becoming solid yellow 2D.

*Shoot color* (*abaxial surfaces*).—Variegated; comprised of yellow 2D striations at and near the margin and fine or thin yellow-green 138B striations concentrated near the midrib; said yellow-green striations extending downward from shoot apex, eventually becoming indistinguishable near the basal half of the shoot, with lower portion of the shoot becoming solid yellow 2D.

*Shoot surface texture.*—Smooth.

Foliage:

*Type.*—Evergreen.

*Arrangement.*—Basal.

*Division.*—Simple.

*Attitude.*—Pendulous and curled.

*Shape.*—Spatulate and elongated.

*Apex.*—Acute.

*Base.*—Sheathed.

*Cross section.*—Concave.

*Venation.*—Parallel.

*Vein color* (*adaxial surfaces*).—Same as surrounding foliage.

*Vein color* (*abaxial surfaces*).—Same as surrounding foliage.

*Margins.*—Entire.

*Attachment.*—Acaulescent.

*Texture.*—Smooth and glossy.

*Surface hairiness* (*adaxial surface*).—Glabrous.

*Surfaces hairiness* (*abaxial surface*).—Glabrous.

*Mature leaf dimensions; outermost leaves.*—Short and broad; length 87 mm, average width 18 mm at widest point.

*Mature leaf dimensions; innermost leaves.*—Long and narrow; length 505 mm, average width 13 mm at widest point.

*Mature leaf dimensions; outermost leaves* (*adaxial & abaxial surfaces*).—Variegated from apex to base; yellow-green (RHS 147A) striations at and near the midrib, striations becoming green 137C moving away from the midrib and further becoming yellow-green 144B at and near the leaf margin. Abaxial surface colors are the same, only with higher glaucosity giving the underside a slight sheen; i.e. silvered appearance.

*Mature leaf dimensions; outermost leaves* (*adaxial & abaxial surfaces*).—Variegated from apex to base; green (RHS 147A) striations at and near the midrib while color striations at and near the margins of the leaf change colors from yellow 4D along the apical half of the leaf and becoming yellow-green 151D along the basal half of the leaf. Abaxial surface colors are the same, only with higher glaucosity giving the underside a slight sheen; i.e. silvered appearance.

*Petiole.*—Leaves are acaulescent; sessile.

*Stipules.*—Absent.

Inflorescence: The inflorescence is a raceme consisting of approximately 80 pedicellate, simple flowers which are freely arranged in axillary fascicles of four. Each fascicle is subtended by a small bract colored yellow green approximately RHS 146A. Raceme length ranges from 8 to 11 cm. Pedicel is 5 mm long and approximately 1 mm wide. Pedicel color is violet 84B. Peduncle length ranges from 19 to 21 cm and the raceme position is at or slightly above the foliage at anthesis. Peduncle color is 79A and transitions to violet 87B at the raceme.

Buds: Obovate flower buds are approximately 4 mm in length and 3 mm in width. Color is violet, RHS 88B.

Flowers: The flowering season is summer to autumn. Perianth is polypetalous with 6 tepals forming a semi-cupped perianth, with a diameter ranging from 6 to 8 mm at anthesis. Mature tepal color is violet 88B and violet 88D at the margin. Margins entire. Apex is obtuse or rounded. Anthers are yellow RHS 6B and stigma is violet RHS 88B. Flowers are persistent and non-fragrant.

Fruit and seeds: Globose berries, approximately 7 mm in diameter, each containing one seed. Berries are glaborous, shiny and have a color that approximates to green 139A when immature and maturing to black 202A late in the season.

COMPARISON OF 'PONTOVIA' WITH OTHER VARIETIES OF *LIRIOPE GIGANTEA*

There are no variegated forms of *Liriope gigantea* known to the breeder. Accordingly, comparison is made to the parent which has a similar size and habit as that of 'Pontovia'. While 'Pontovia' is similar to common *Liriope gigantea* in many characteristics, its variegated foliage, taller inflorescence and darker violet flowers clearly distinguish it from the species.

'Pontovia' has a wide array of foliage variegation colors as herein described while the foliage of the species is solid yellow-green (RHS 147A). Also, the inflorescence of 'Pontovia' sit higher above the foliage than that of the species due to the fact that it has a longer peduncle and a larger raceme; the typical inflorescence of 'Pontovia' ranges from 19 to 21 cm in length whereas the inflorescence of the species ranges from 15 to 18 cm long. Furthermore, the flowers of 'Pontovia' are a darker shade of violet when compared to the species; the primary flower color of 'Pontovia' is violet 88B whereas the flower color of the species approximates to 85B.

The combination of multicolored leaf variegation, large inflorescence and dark violet flowers makes 'Pontovia' a desirable ornamental plant suited for mass production for container and landscape use.

That which is claimed is:

1. A new and distinct variety of *Liriope gigantea* plant named 'Pontovia', substantially as described and illustrated herein.

* * * * *